(12) United States Patent
Irani

(10) Patent No.: US 6,783,677 B1
(45) Date of Patent: Aug. 31, 2004

(54) ANAEROBIC FILM BIOGAS DIGESTER SYSTEM

(75) Inventor: Mayyar F. Irani, Selinsgrove, PA (US)

(73) Assignee: Mayyar Systems, Inc., Selinsgrove, PA (US)

( * ) Notice: Subject to any disclaimer, the term of this patent is extended or adjusted under 35 U.S.C. 154(b) by 0 days.

(21) Appl. No.: 10/361,514

(22) Filed: Feb. 6, 2003

(51) Int. Cl.$^7$ .................................................. C02F 3/28
(52) U.S. Cl. ....................... 210/603; 210/612; 210/615; 210/260; 435/262.5
(58) Field of Search ................................. 210/603, 612, 210/613, 615, 252, 259, 260; 435/262, 262.5

(56) References Cited

U.S. PATENT DOCUMENTS

| | | | |
|---|---|---|---|
| 3,242,055 A | * | 3/1966 | De Lucia .................... 435/176 |
| 3,607,737 A | | 9/1971 | Gamer |
| 4,356,269 A | * | 10/1982 | Thomsen et al. ......... 435/290.2 |
| 4,375,412 A | | 3/1983 | Schimel |
| 4,493,770 A | | 1/1985 | Moilliet |
| 4,521,310 A | | 6/1985 | Casey |
| 4,579,645 A | * | 4/1986 | Uemura et al. ............... 208/23 |
| 4,594,078 A | | 6/1986 | Guerin et al. |
| 4,927,530 A | | 5/1990 | Ueda |
| 5,085,766 A | | 2/1992 | Born |
| 5,525,229 A | | 6/1996 | Shih |
| 5,554,301 A | | 9/1996 | Rippetoe et al. |
| 5,560,819 A | | 10/1996 | Taguchi |
| 6,015,496 A | * | 1/2000 | Khudenko ................... 210/603 |

FOREIGN PATENT DOCUMENTS

FR           266901 A1 * 5/1992

* cited by examiner

Primary Examiner—Fred G. Prince
(74) Attorney, Agent, or Firm—Schmeiser, Olsen & Watts

(57) ABSTRACT

An anaerobic digester for digesting a slurry of organic waste comprising: a tank having an outer side wall and a lower inner wall, a first radiant heating floor between the outer wall and a first side of the inner wall forming a first chamber and a second radiant heating floor between the outer wall and a second and opposite side of the inner wall forming a second chamber, an inlet pipe for delivering the slurry to a lower portion of the first chamber and a outlet pipe for removing digested slurry from a lower portion of the second chamber, the slurry maintained at a depth that is greater than a height of the inner wall; and a gas collection chamber sealed to the tank along the length of the upper surface of the outer wall.

51 Claims, 10 Drawing Sheets

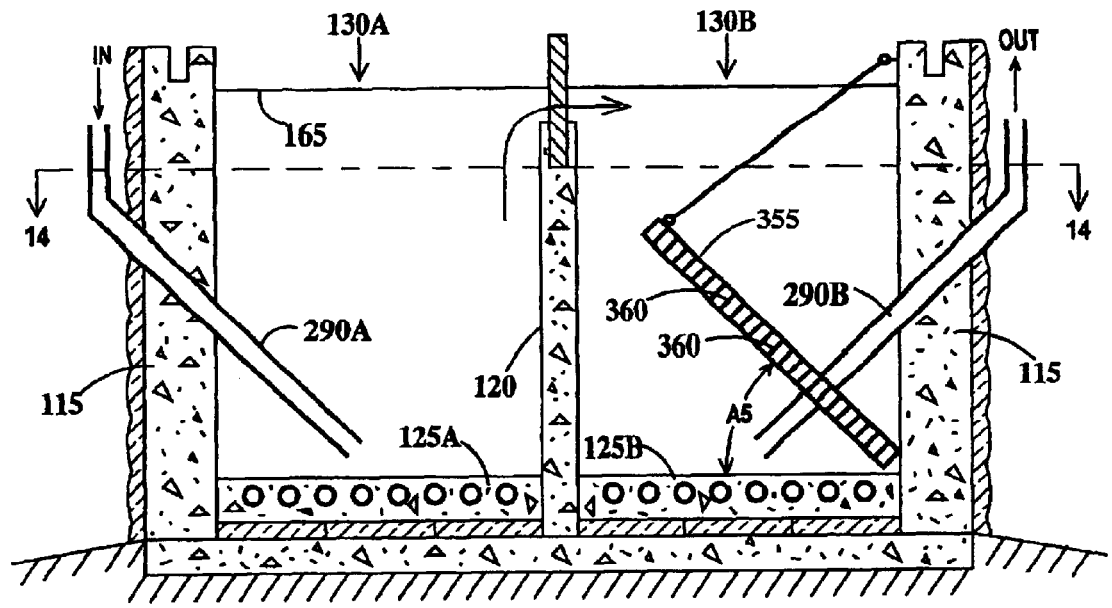
FIG. 13
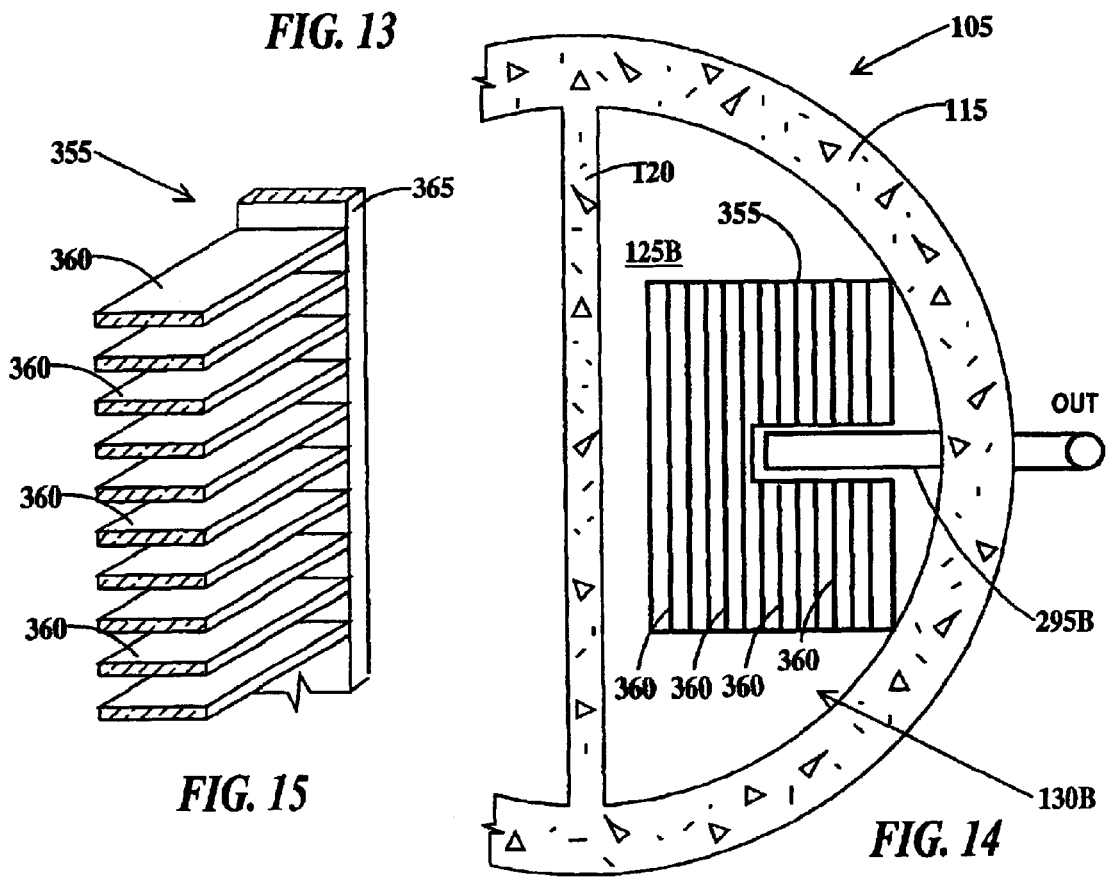
FIG. 15
FIG. 14

ANAEROBIC FILM BIOGAS DIGESTER SYSTEM

FIELD OF THE INVENTION

The present invention relates to the field of bio-methane production by anaerobic digestion of organic material and more specifically, it relates to an apparatus and system for the production of bio-methane from organic substances contained in animal or vegetable waste.

BACKGROUND OF THE INVENTION

The management of nutrients contained in animal waste (manure) and vegetable waste is a continuing concern for managers of livestock operations. If mishandled, such wastes can contaminate water supplies with nitrogen and phosphorous salts and organics and microorganisms. One method to control potential contamination is by anaerobic digestion. Anaerobic digestion of organic material, such as animal and agricultural waste is the fermentation of such material by bacteria in the absence of oxygen. However, while various anaerobic digestion processes such as plug-flow and lagoon designs are being practiced, there remains a need for an improved anaerobic digestion that is more efficient and cost-effective then those currently practiced.

SUMMARY OF THE INVENTION

A first aspect of the present invention is an anaerobic digester for digesting a slurry of organic waste comprising: a tank having a vertical outer side wall and a vertical lower inner wall, the outer wall and inner wall each having a top surface, a first radiant heating floor between the outer wall and a first side of the inner wall forming a first chamber and a second radiant heating floor between the outer wall and a second and opposite side of the inner wall forming a second chamber, the first radiant heating floor maintaining the slurry in the first chamber at a first temperature and the second radiant heating floor maintaining the slurry in the second chamber at a second temperature; an inlet pipe for delivering the slurry to a lower portion of the first chamber and a outlet pipe for removing digested slurry from a lower portion of the second chamber, the slurry maintained at a depth that is greater than a height of the inner wall; and a gas collection chamber sealed to the tank along the length of the upper surface of the outer wall.

A second aspect of the present invention is a method for digesting a slurry of organic waste comprising: providing a tank having a vertical outer side wall and a vertical lower inner wall, the outer wall and inner wall each having a top surface, a first radiant heating floor between the outer wall and a first side of the inner wall forming a first chamber and a second radiant heating floor between the outer wall and a second and opposite side of the inner wall forming a second chamber, the first radiant heating floor maintaining the slurry in the first chamber at a first temperature and the second radiant heating floor maintaining the slurry in the second chamber at a second temperature; delivering the slurry to an inlet pipe extending into a lower portion of the first chamber; delivering the slurry to an inlet pipe extending into a lower portion of said first chamber; removing digested slurry through an outlet pipe extending into a lower portion of the second chamber; and collecting biogas in a gas collection chamber sealed to the tank along the length of the upper surface of the outer wall.

A third aspect of the present invention is a system for digesting a slurry of organic waste comprising: (a) a preheat tank for preheating the slurry before introducing the slurry to a digester; (b) the digester comprising: a tank having a vertical outer side wall and a vertical lower inner wall, the outer wall and inner wall each having a top surface, a first radiant heating floor between the outer wall and a first side of the inner wall forming a first chamber and a second radiant heating floor between the outer wall and a second and opposite side of the inner wall forming a second chamber, the first radiant heating floor maintaining the slurry in the first chamber at a first temperature and the second radiant heating floor maintaining the slurry in the second chamber at a second temperature; an inlet pipe for delivering the slurry to a lower portion of the first chamber and a outlet pipe for removing digested slurry from a lower portion of the second chamber, the slurry maintained at a depth that is greater than a height of the inner wall; and a gas collection chamber for collecting gas, the gas collection chamber sealed to the tank along the length of the upper surface of the outer wall; (c) an engine coupled to a generator, the engine generating heat by burning the gas collected in the gas collection chamber and driving the generator in order to generate electricity; and (d) a heat exchanger for taking the heat generated by the engine, heating a fluid with the heat and supplying the heated fluid to the preheat tank and the first and second radiant floors.

BRIEF DESCRIPTION OF DRAWINGS

The features of the invention are set forth in the appended claims. The invention itself, however, will be best understood by reference to the following detailed description of an illustrative embodiment when read in conjunction with the accompanying drawings, wherein:

FIG. 13 is a cross-sectional side view of the tank portion of the anaerobic digester illustrating an alternative method of enhanced bacteria growth according to the present invention;

FIG. 14 is a top cross-sectional view through line 14—14 of FIG. 13;

FIG. 15 is an isometric view of a portion of the filaments and frame of FIGS. 13 and 14.

DETAILED DESCRIPTION OF THE INVENTION

Figure 1:
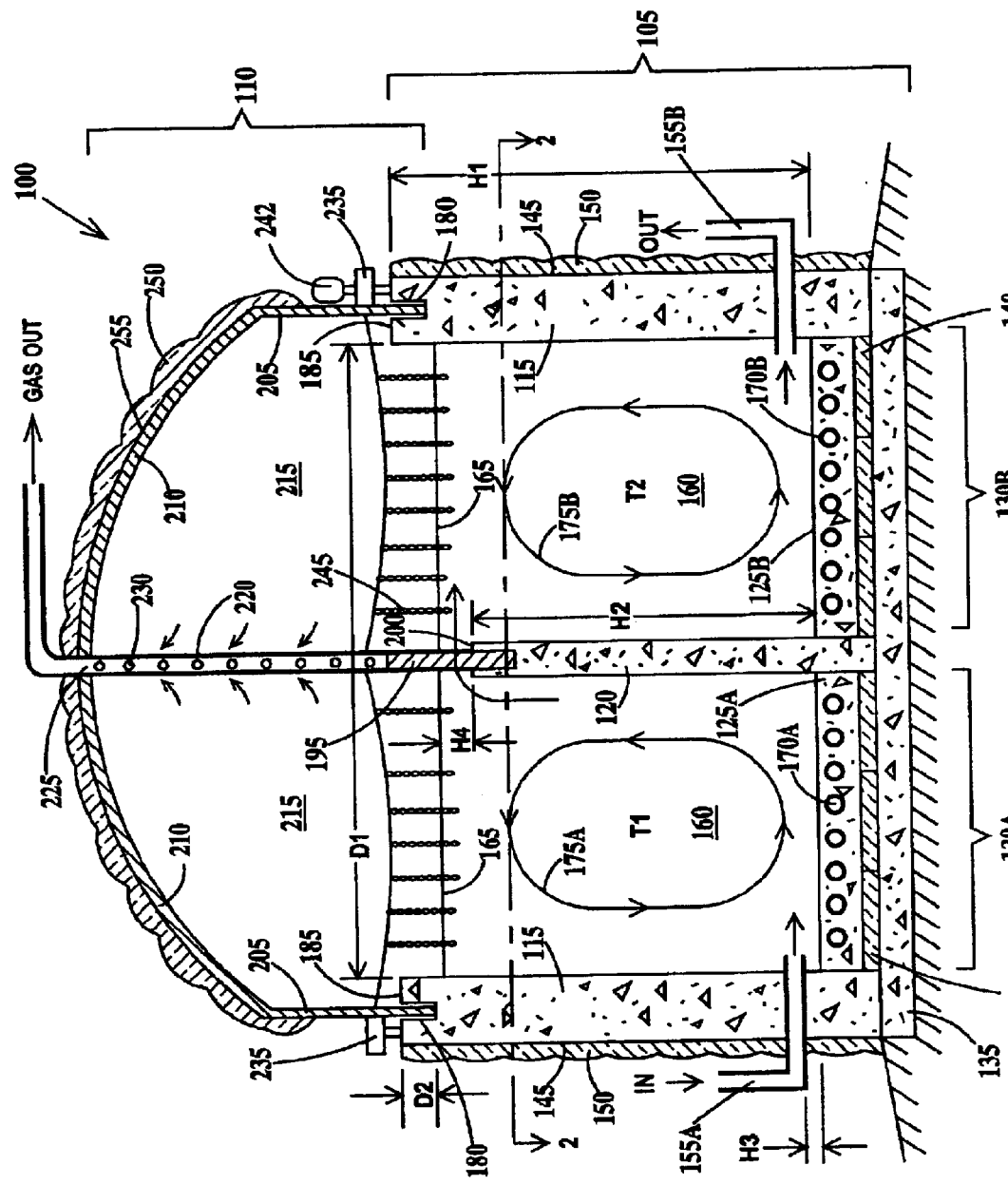
FIG. 1 is cross-sectional side view of an anaerobic digester according to the present invention.

FIG. 1 is cross-sectional side view of an anaerobic digester according to the present invention. In FIG. 1, digester 100 includes a tank 105 and a cover 110. Tank 105 includes a circular outer wall 115 (see FIG. 2) and an integral internal dividing wall 120. A first radiant heating floor 125A, outer wall 115 and dividing wall 120 define a first chamber 130A and a second radiant heating floor 125B, outer wall 115 and dividing wall 120 define a second chamber 130B. Thus, tank 105 is divided into two internal chambers. Outer wall 115 and dividing wall 120 are supported by a sub-floor 135. Structural foam insulating panels 140 are located between first and second radiant heating floors 125A and 125B and sub-floor 135 to prevent heat loss into the earth. In one example, panels 140 are about 1 to 2 inches thick. An outer surface 145 of outer wall 115 is covered with sprayed foam insulation 150 to prevent heat loss to the air. Except in very warm climates, heat loss through the earth or air can drastically slow down the anaerobic digestion process and methane production carried out in tank 105.

Outer wall 115 has a height H1 and dividing wall 120 has a height H2 above first and second radiant floors 125A and 125B, where H1 is may be greater than H2. Tank 105 has a diameter D1. In one example, H2 is three quarters H1. In one example, D1 is about 15 to 40 feet, H1 is about 10 to 20 feet and H2 is about 5 to 18 feet. In one example, outer wall 115 is constructed from concrete and is about 8 to 12 inches thick, dividing wall 120 is also constructed from concrete and is about 6 to 12 inches thick, sub-floor 135 is also constructed from concrete and is about 4 to 10 inches thick and first and second radiant floors 125A and 125B are constructed from concrete and are 4 to 10 inches thick. In another example, outer wall 115 and dividing wall 120 may be fabricated from treated steel, fiberglass or plastic.

An inlet pipe 155A passing through outer wall 115 into first chamber 130A at a height H3 above radiant floor 125A brings an organic slurry 160 into the first chamber. In one example, slurry 160 is liquefied manure and in a second example, slurry 160 is liquefied vegetable matter. A manure-based slurry contains three types of naturally occurring anaerobic bacteria. The first type is a liquefying bacteria that converts carbohydrates, proteins and fats into soluble compounds such as sugars. The second type is an acid-forming bacteria that converts the soluble compounds into volatile organic acids and carbon dioxide. The third type of bacteria produces methane from the volatile organic acids. Slurry 160 is further discussed infra in reference to FIG. 16. Both inlet pipe 155A and outlet pipe 155B pass through outer wall 115 at the point that outer wall 115 is furthest from dividing wall 120. Slurry 160 overflows dividing wall 120 into second chamber 130B. An outlet pipe 155B passing through outer wall 115 into second chamber 130B at height H3 removes processed slurry 160 from the second chamber. However, the surface 165 of slurry 160 is maintained at a level H4 above dividing wall 120. In one example, H3 is about 1 to 3 feet and H4 is about 1 to 3 feet. In no case is slurry 160 allowed to reach a height sufficient to overflow outer wall 115.

First and second radiant heating floors 125A and 125B includes a first set of heating tubes 170A and second set of heating tubes 170B respectively. A heated fluid, for example, water, antifreeze, a water/antifreeze mix or air is forced through each set of heating tubes 170A and 170B. A higher temperature fluid is supplied to first set of heating tubes 170A than is supplied to second set of heating tubes 170B, thus maintaining first chamber 130A at a temperature T1 and second chamber 130B at a temperature T2, where T1 may be greater than T2. Radiant heating floor 125A sets up a first convection circulation 175A in slurry 160 in first chamber 130A. Due to T1 greater than T2, slurry 160 moves upwards along dividing wall 120 and into second chamber 130B. A portion of slurry 160 circulates back toward outer wall 115 in first chamber 130A. Another portion of slurry 160 flows over dividing wall 120 and into second chamber 130B as stated supra. A second convection circulation 175B is set up in slurry 160 on second chamber 130B due to radiant heating floor 125B. Both first and second convection currents 175A and 175B serve to mix and enhance digestion of slurry 160 in the respective first and second chambers 130A and 130B.

In one example, T1 is about 70° F. to 120° F. and T2 is about 65° F. to 115° F. wherein T1–T2 is about 5° F. to 10° F. For maximum volatile organic acids production, T1 is about 95° F. to 105° F. and for maximum methane production T2 is about 90° F. to 100° F. The dual chamber design of digester 100, thus allows maximization of both processes, which is not possible in a single chamber tank. It is also possible to maintain T1=T2 or to alternate between T1>T2 and T1=T2.

A slot 180 is formed in a top surface 185 of outer wall 115. Slot 180 has a depth of D2. In one example, D2 is about 2 to 3 feet. A pin 195 extends from a top surface 200 of inner wall 120. Both slot 180 and pin 195 form part of the support structure for top 110.

Top 110 includes a circular sidewall 205 and a dome 210 attached to the sidewall. Sidewall 205, dome 210 and top surface 165 of slurry 160 define a gas collection chamber 215. Sidewall 205 is positioned in slot 180 and floats on a fluid filling the slot. The relationship between slot 180 and sidewall 205 is further discussed infra in reference to FIG. 1A. A gas collection pipe 220 is fixedly connected to a center 225 of dome 210, extends downward from a center 225 of dome 210 and engages pin 195. The relationship between gas collection pipe 220 and pin 195 is further discussed infra in reference to FIG. 1B. Gas collection pipe 220 includes a multiplicity of through holes 230. Gas generated by digester 100 enters gas collection pipe 220 through holes 230 and is extracted. Top 110 is thus free to rotate in slot 180 and move up and down in slot 180 relative to surface 165 of slurry 160 in response to changes in the volume of the gas (not shown) thus maintaining a more stable gas outlet pressure. Slot 180 is filled with oil and the oil acts as a biogas and airtight seal (see FIG. 1A). The oil seal keeps out oxygen, thus maintaining an anaerobic atmosphere.

Top 110 is guided in both up and down motion and rotation motion by a multiplicity of guide wheels 235 mounted on top surface 185 of outer wall 115. A motor 242 mounted to one wheel 235 enables rotation of top 110 about a vertical axis passing through center 225. A set of chains 245, is suspended inside of top 110 and extend into slurry 160. When top 110 is rotated, chains 245 break up any crust forming on top surface of slurry 160 releasing any gas trapped underneath the crust.

In one example, top 110 may be fabricated from treated steel, fiberglass or plastic. A layer of spray foam insulation 250 is formed on an outer surface 255 of top 110 to prevent heat loss to the air.

Figure 1A:
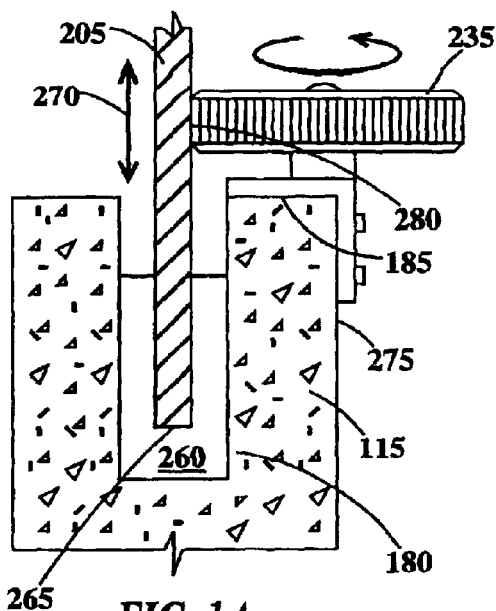
FIGS. 1A and 1B illustrate details of the rotation of the top of the digester according to the present invention.
Figure 1B:
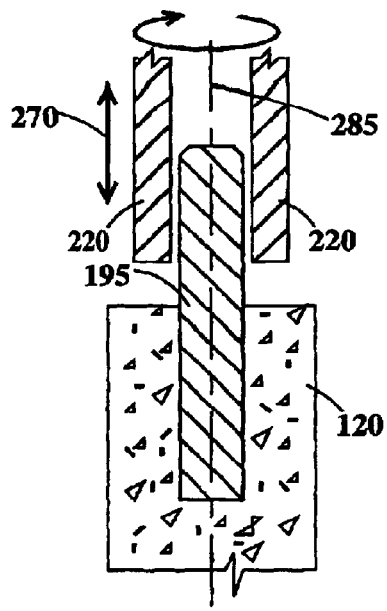

FIGS. 1A and 1B illustrate details of the rotation of the top of the digester according to the present invention. In FIG. 1A, slot 180 in outer wall 115 is filled with oil 260. In one example, oil 260 is vegetable oil or another, non-petroleum derived oil, such as silicon oil. A lower surface 265 of sidewall 205 is submerged in oil 260. As described supra, top 110 (see FIG. 1) is free to move in the vertical direction 270 and top 110 floats in oil 260. Oil 260 also acts as an airtight seal between top 110 and tank 105 (see FIG. 1). Guide wheels 235 are mounted on an outer surface 275 of wall 115. Guide wheels 235 contact an outer surface 280 of sidewall 205. Wheels 235 keep sidewall 205 substantially centered in slot 180 and stop sidewall 205 from contacting outer wall 115.

In FIG. 1B, pin 195 having a longitudinal axis 285, which is aligned with center 225 (see FIG. 1), is partially embedded in dividing wall 120. Gas collection pipe 220 is free to slide in the vertical direction 270 as well as rotate about axis 285, as top 110 (see FIG. 1) rotates about axis 285.

Figure 2:
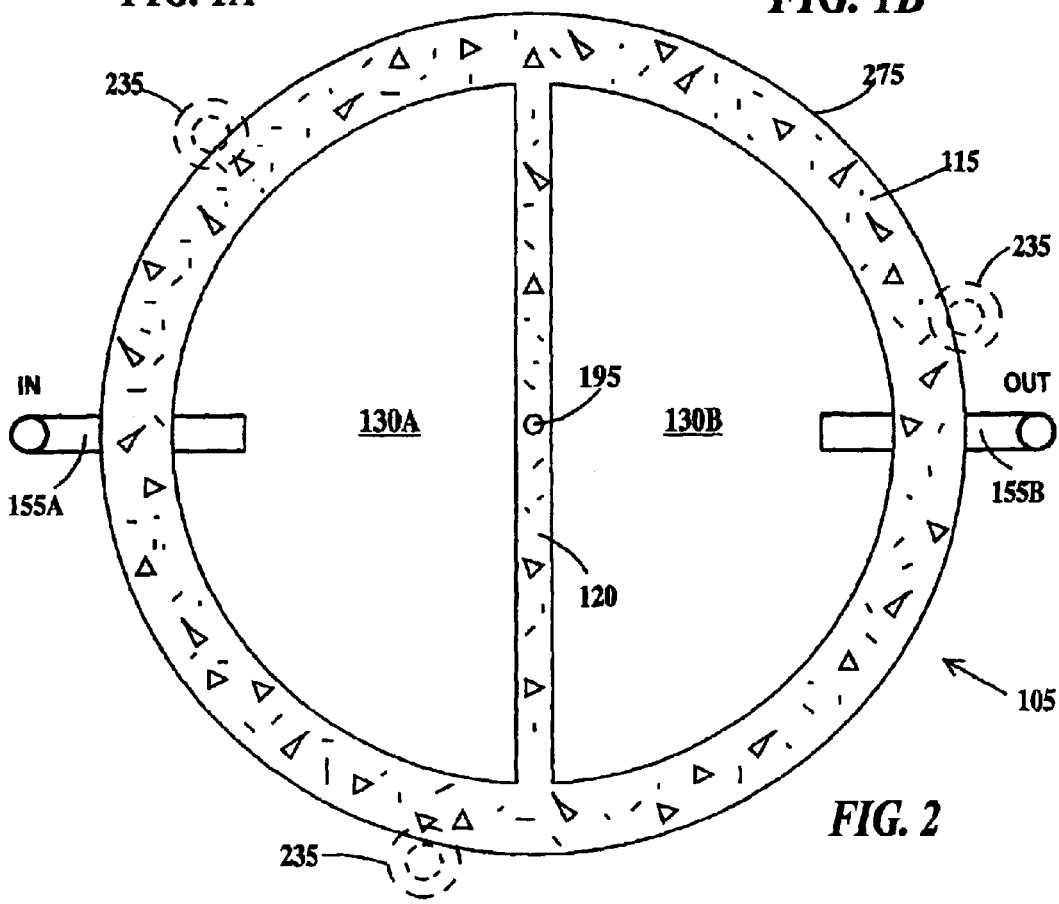
FIG. 2 is a top cross-sectional view through line 2—2 of FIG. 1.

FIG. 2 is a top cross-sectional view through line 2—2 of FIG. 1. In FIG. 2, dividing wall 120 divides tank 105 into identical semi-circular first and second chambers 130A and 130B. However, it may be desirable to for dividing wall 120 to divide tank 105 into two unequal chambers by moving dividing wall toward either inlet pipe 155A or outlet pipe 155B. Pin 195 is located in the center of dividing wall 120 (and in the center of tank 105), equally distant from any point on outer wall 115. Three equally spaced guide wheels 235 (dashed lines) are shown to indicate their relative position to each other and to pin 195. Each guide wheel 235 is spaced one-third the perimeter along outer surface 275 of outer wall 115. More than three guide wheels 235 may be used. As mentioned supra, one drive wheel 235 is fitted with a motor for rotating top 110 (see FIG. 1).

Figure 3:
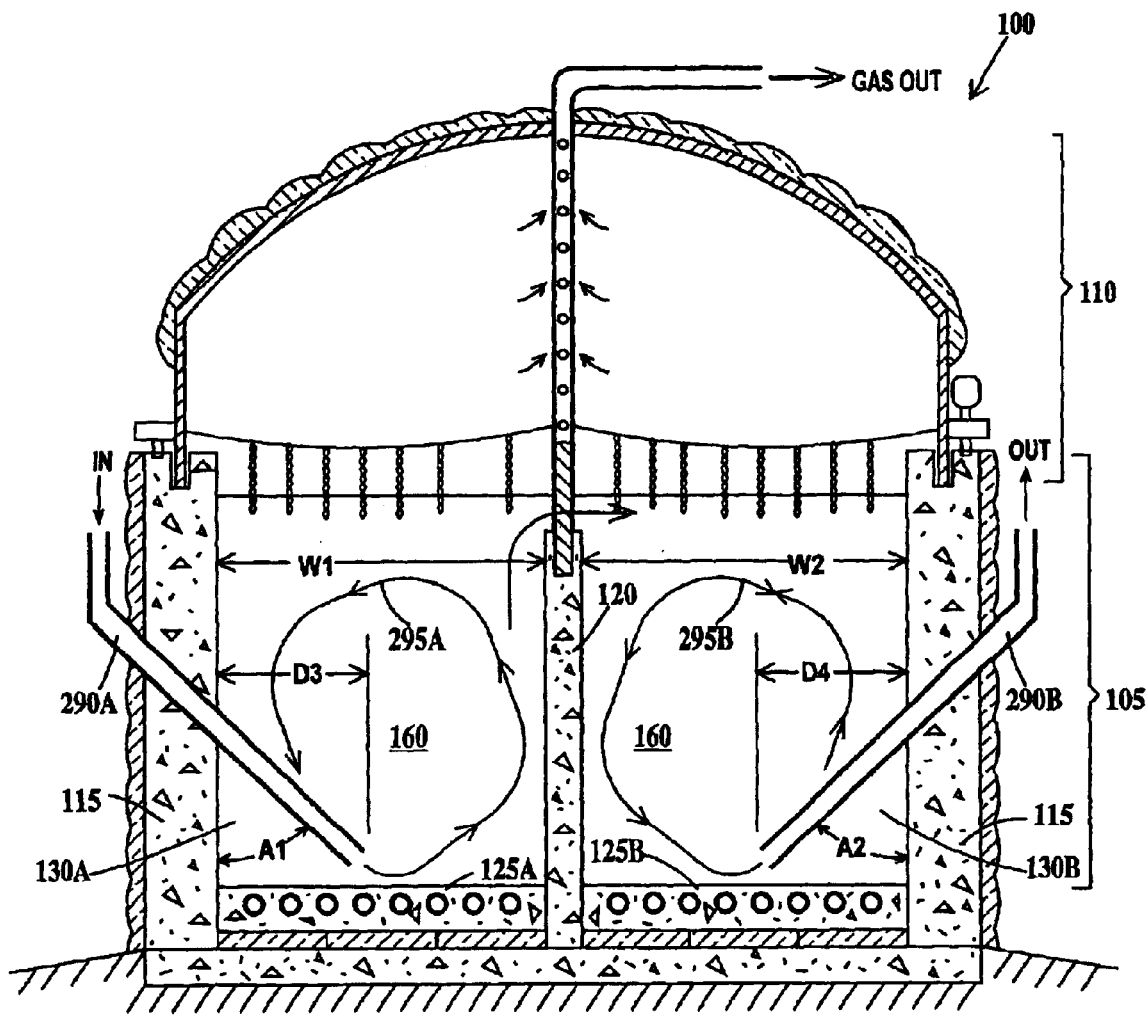
FIG. 3 is cross-sectional side view of the anaerobic digester of FIG. 1, illustrating an alternative method of organic material in-feed and out-feed according to the present invention.

FIG. 3 is cross-sectional side view of the anaerobic digester of FIG. 1, illustrating an alternative method of organic material in-feed and out-feed according to the present invention. FIG. 3 is similar to FIG. 1 except inlet pipe 290A and outlet pipe 290B replace inlet pipe 155A and outlet pipe 155B of FIG. 1 respectively. Both inlet pipe 290A and outlet pipe 290B pass through outer wall 115 at the point that outer wall 115 is furthest from dividing wall 120. Inlet pipe 290A projects into first chamber 130A at an angle A1 and a distance D3 from outer wall 115. First chamber 130A has a width W1 at its widest point. In one example, A1 between about 30° and 60° and D3 is one half W1. Outlet pipe 290B projects into second chamber 130B at an angle A2 and a distance D4 from outer wall 115. Second chamber 130B has a width W2 at its widest point. In one example, A2 is 45° and D4 is one half W2. W1 may equal W2 or may not equal W2. D3 may equal D4 or may not equal D4. A1 may equal A2 or may not equal A2. Angling input pipe 290A and outlet pipe 290B sets up a circulations 295A and 295B in slurry 160 in first chamber 130A and second chamber 130B respectively that aid in mixing and enhancing digestion of slurry 160.

Figure 3A:
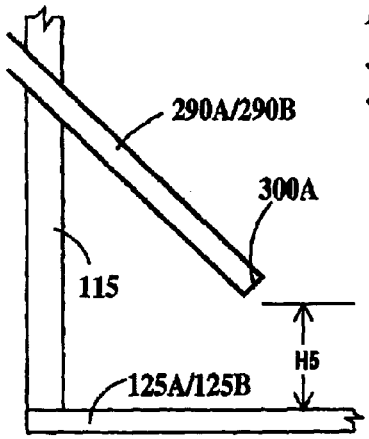
FIGS. 3A, 3B and 3C illustrate alternative details of the alternative in-feed and out-feed of FIG. 3.
Figure 3B:
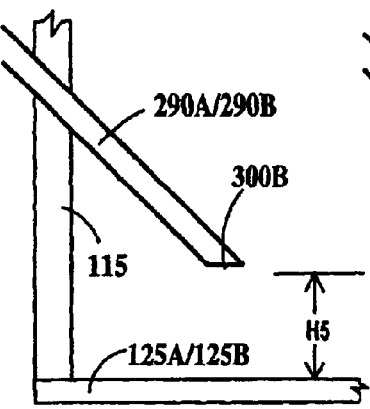
Figure 3C:
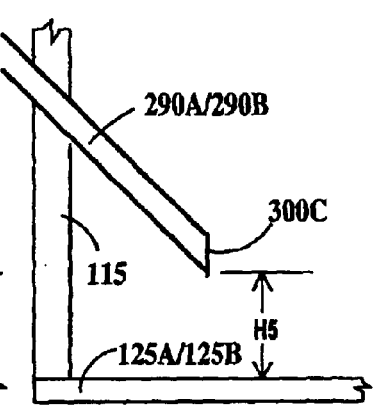

FIGS. 3A, 3B and 3C illustrate alternative details of the alternative in-feed and out-feed of FIG. 3. In FIG. 3A, an end 300A of inlet pipe 290A (or outlet pipe 290B) is cut perpendicular to its length. In FIG. 3B, an end 300B of inlet pipe 290A (or outlet pipe 290B) is cut parallel to first radiant heating floor 125A (or second radiant floor 125B). In FIG. 3C, an end 300C of inlet pipe 290A (or outlet pipe 290B) is cut perpendicular to its length to first radiant heating floor 125A (or second radiant floor 125B). In all three FIGS. 3A, 3B, and 3C, inlet pipe 290A (or outlet pipe 290B) terminates a distance H5 above first radiant heating floor 125A (or second radiant floor 125B). In one example, H5 is about 1 to 3 feet.

Figure 4:
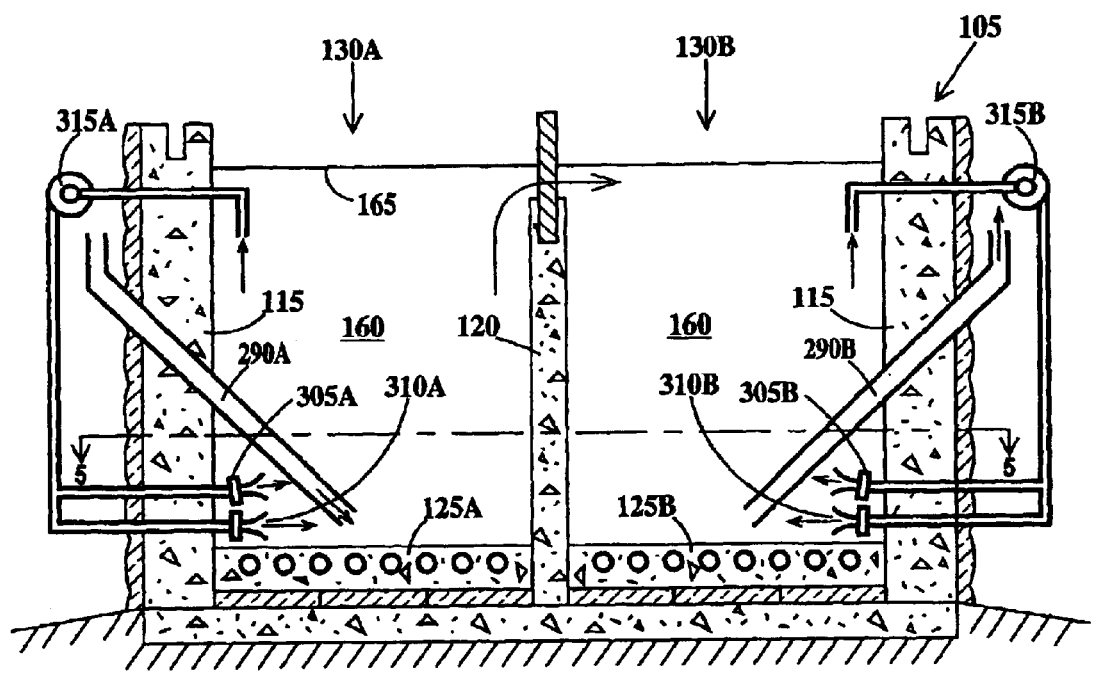
FIG. 4 is a cross-sectional side view of the tank portion of the anaerobic digester illustrating a method of waste slurry mixing according to the present invention.
Figure 6:
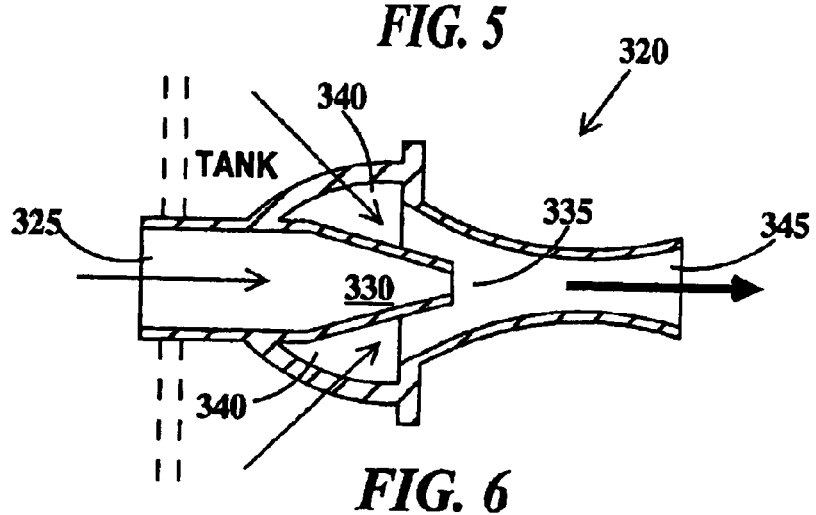
FIG. 6 is a cross-sectional side view of an eductor.

FIG. 4 is a cross-sectional side view of the tank portion of the anaerobic digester illustrating a method of waste slurry 160 mixing according to the present invention. In FIG. 4, tank 105 is similar to tank 105 illustrated in FIG. 3 and described supra except for the addition of a first upper eductor 305A, first lower eductors 310A (there are two, but only one is illustrated), a first eductor pump 315A and connecting pipes for respectively mixing and sweeping first chamber 130A and for the addition of a second upper eductor 305B, second lower eductors 310B (there are two, but only one is illustrated), a second eductor pump 315B and connecting pipes for respectively mixing and sweeping second chamber 130B. A typical eductor is illustrated in FIG. 6 and described infra.

In FIG. 4, first upper eductor 305A and first lower eductors 310A are located adjacent to first radiant heating floor 125A near the bottom of first chamber 130A. First eductors 305A and 310A are supplied with slurry 160 taken from the top of first chamber 130A adjacent to top surface 165 of slurry 160 by first eductor pump 315A. Similarly, second upper eductor 305B and second lower eductors 310B are located adjacent to second radiant heating floor 125B near the bottom of second chamber 130B. Second eductors 305B and 310B are supplied with slurry 160 taken from the top of second chamber 130B adjacent to top surface 165 of slurry 160 by second eductor pump 315B.

While tank 105 is illustrated using angled input and output pipes 290A and 290B respectively, the straight inlet and outlet pipes 155A and 155B respectively (see FIG. 1) may be used in conjunction with eductors.

Figure 4A:
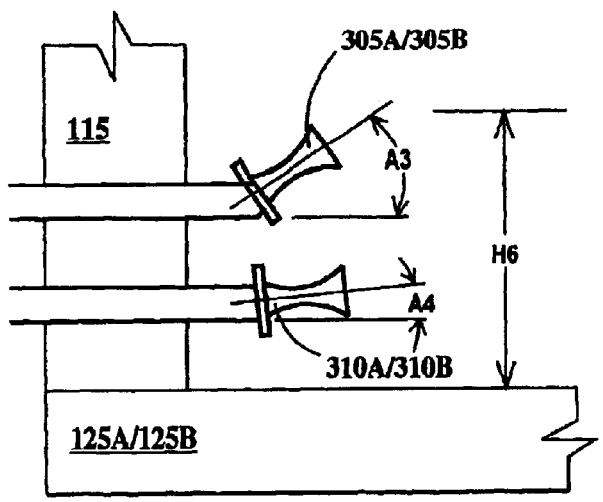
FIGS. 4A and 4B illustrate positioning of the eductors illustrated in FIG. 3.
Figure 4B:
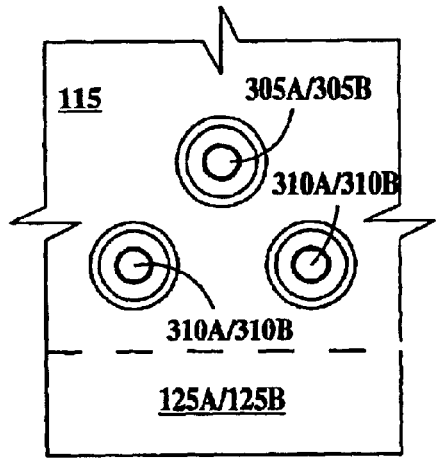

FIGS. 4A and 4B illustrate positioning of eductors 305A, 310A, 305B and 310B illustrated in FIG. 3. In FIG. 4A, first upper eductor 305A (or second upper eductor 305B) is mounted at an angle A3 relative to first radiant heating floor 125A (or second radiant heating floor 125B). First lower inductors 310A (or second lower eductors 310B) are mounted at an angle A4 relative to first radiant heating floor 125A (or second radiant heating floor 125B). Upper eductors 305A and 305B provide mixing of slurry 160 (and breaking up of any crust formed on top surface 165 of slurry 160 (see FIG. 4) while lower eductors 310A and 310B sweep the bottom of first and second chambers 130A and 130B respectively to force any solids that have settled out of slurry during the digestion process to be re-dispersed in slurry 160.

In one example, A3 is about 40° to 60° and A4 is about 2° to 5°. Eductors 305A, 310A, 305B and 310B are all mounted within a distance H6 of first or second radiant floor 125A and 125B. In one example, H6 is about 1 to 5 feet.

In FIG. 4B, it is clear that first lower eductors 310A are located to either side of first upper eductor 305A and second lower eductors 310B are located to either side of second upper eductor 305B.

Figure 5:
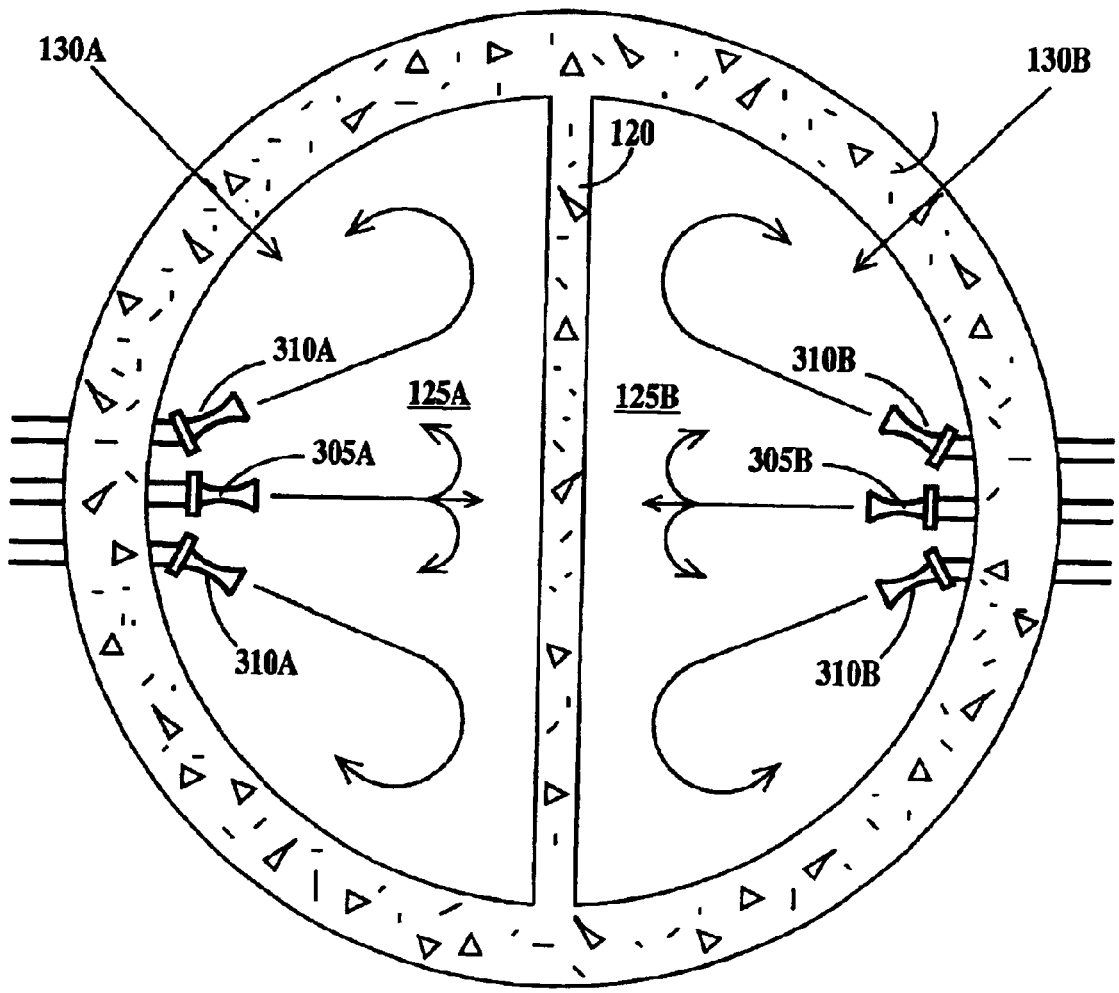
FIG. 5 is a top cross-sectional view through line 5—5 of FIG. 4.

FIG. 5 is a top cross-sectional view through line 5—5 of FIG. 4. In FIG. 5, the mixing pattern generated by first upper eductor 305A in first chamber 130A, which is directed upward toward dividing wall 120 is as illustrated and the mixing pattern generated by second upper eductor 305B in second chamber 130B, which is directed upward toward dividing wall 120 is as illustrated. The sweeping pattern generated by first lower eductors 310A in first chamber 130A, which is directed very slightly upward, but flows mainly along first radiant floor 125A toward dividing wall 120 is as illustrated and the mixing pattern generated by second lower eductors 310B in second chamber 130B, which is directed very slightly upward, but flows mainly along second radiant floor 125B toward dividing wall 120 is as illustrated.

Slurry 160 is not pumped through eductors 305A, 305B, 310A and 310B continually, but rather on a periodic basis for fixed durations of time. In one example, if the total digestion time is 28 days, slurry 160 is pumped once every 7 days for several hours.

FIG. 6 is a cross-sectional side view of an eductor. In FIG. 6, eductor 320 includes an inlet 325 (supplied from a pump outside of the tank), a venturi 330, a mixing chamber 335 where liquid within the tank drawn in from side vents 340 and mixed with liquid supplied by the pump and an outlet 345 for discharging the mixture. Typical eductors will draw in 4 gallons of liquid through side vents 340 for each gallon of liquid flowing through venturi 330.

Figure 7:
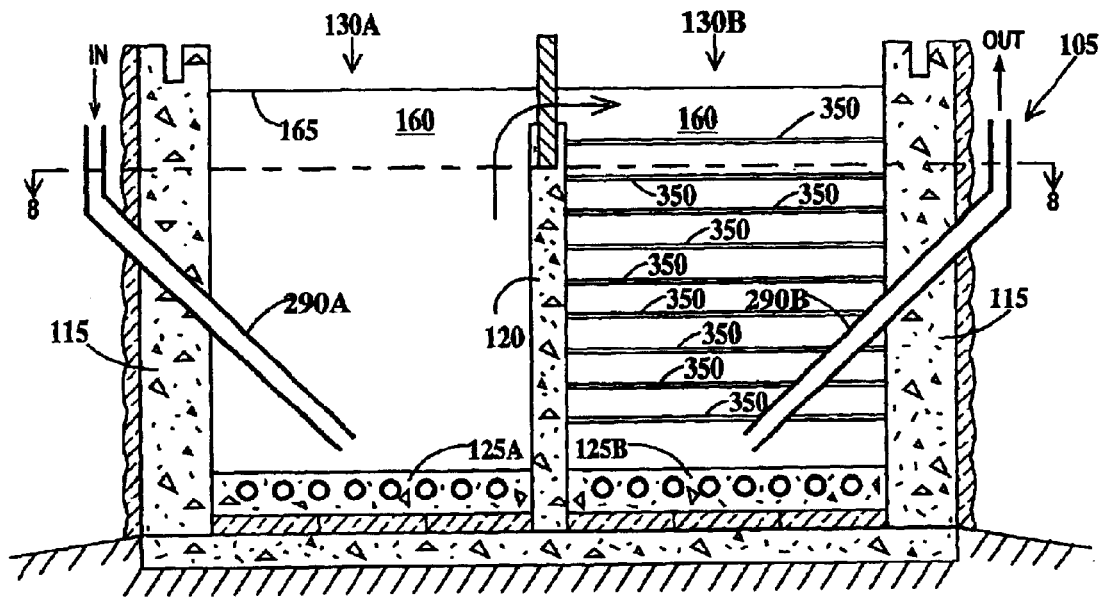
FIG. 7 is a cross-sectional side view of the tank portion of the anaerobic digester illustrating a method of enhanced bacteria growth according to the present invention.
Figure 8:
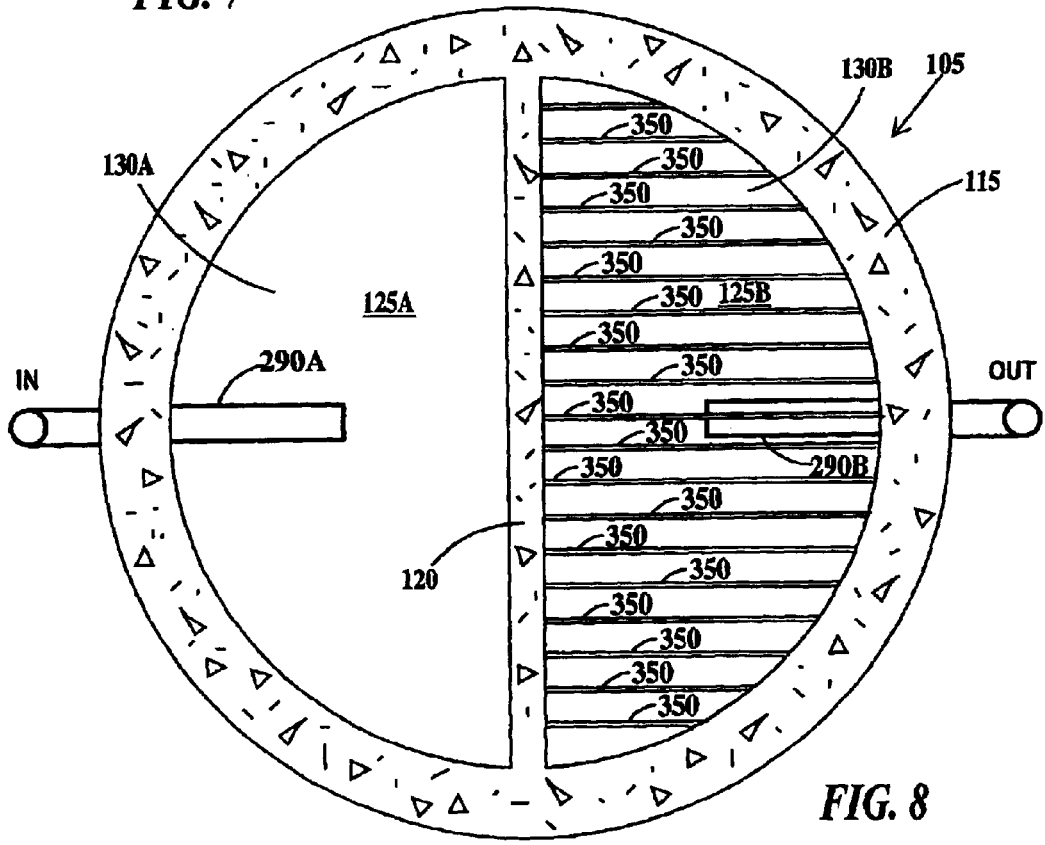
FIG. 8 is a top cross-sectional view through line 8—8 of FIG. 7.

FIG. 7 is a cross-sectional side view of the tank portion of the anaerobic digester and FIG. 8 is a top cross-sectional view through line 8—8 of FIG. 7 illustrating a method of enhanced bacteria growth according to the present invention. In FIGS. 7 and 8, filaments 350 are immersed in several layers in slurry 160 in second chamber 130B of tank 105. Each filament is connected between dividing wall 120 and outer wall 115. Each filament extends perpendicular to dividing wall 120 and is orientated about parallel to radiant floor 125B. Alternatively, filaments 350 may be orientated at angles up to about 60° relative to radiant floor 125B. Additionally, filaments 350 may all be orientated in the same direction or in different directions. Filaments 350 provide a substrate for colonization by naturally occurring bacteria found in slurry 160. By providing sites for bacteria colonization, digestion of slurry 160 is enhanced. Enhancing digestion is defined as increasing slurry 160 digestion rate or gas production rate or both.

Figure 9:
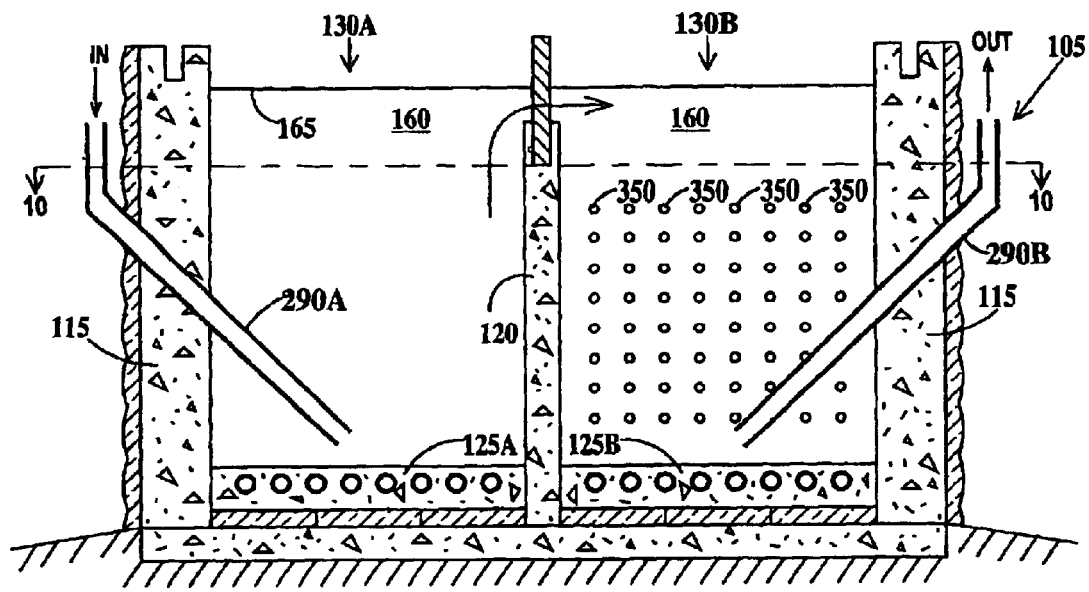
FIG. 9 is a cross-sectional side view of the tank portion of the anaerobic digester illustrating an alternative arrangement of filaments.
Figure 10:
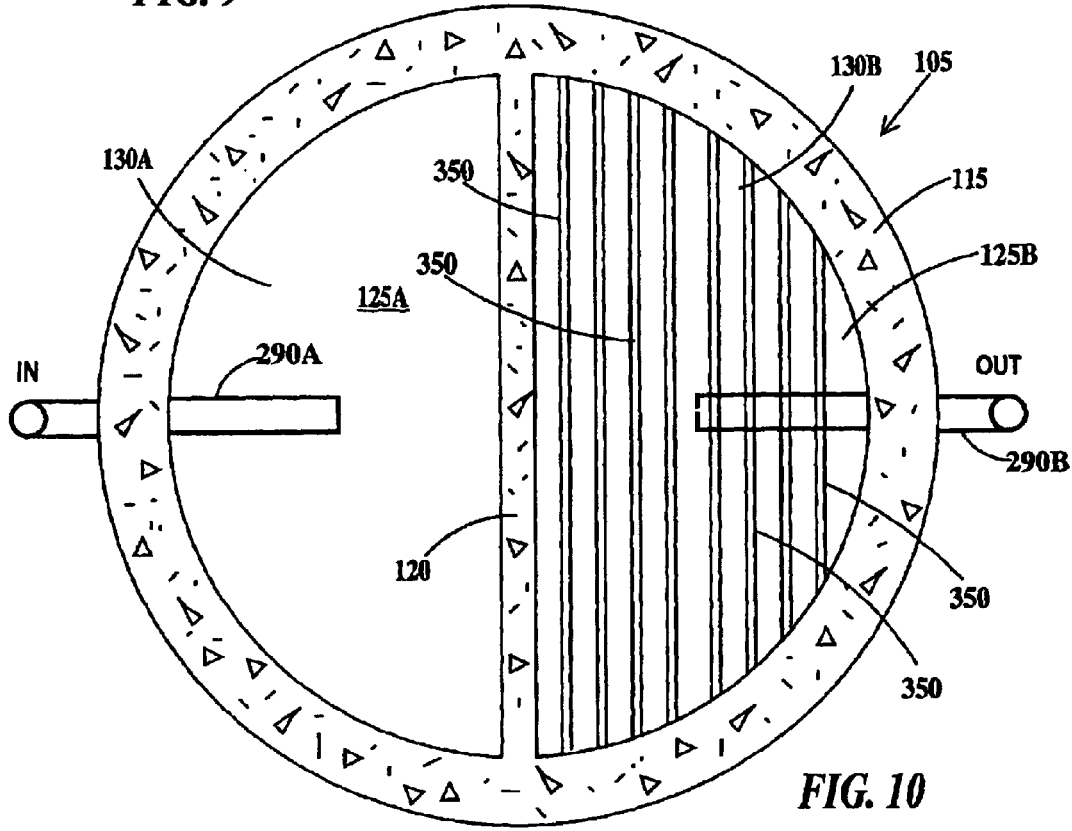
FIG. 10 is a top cross-sectional view through line 10—10 of FIG. 9.

FIG. 9 is a cross-sectional side view of the tank portion of the anaerobic digester and FIG. 10 is a top cross-sectional view through line 10—10 of FIG. 9 illustrating a an alternative arrangement of filaments 350. In FIGS. 9 and 10, filaments 350 are immersed in several layers into slurry 160 in second chamber 130B of tank 105. Each filament is connected between opposite sides of outer wall 115. Each filament extends parallel to dividing wall 120. It is possible to have some filaments 350 orientated as illustrated in FIG. 10 and others as illustrated in FIG. 8 and described supra.

Figure 11A:
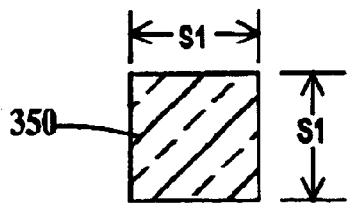
FIGS. 11A, 11B and 11C are cross-sectional views of alternative filament geometries.
Figure 11B:
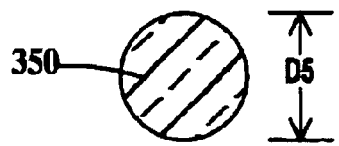
Figure 11C:
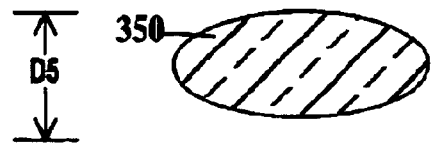

FIGS. 11A, 11B and 11C are cross-sectional views of alternative filament 350 geometries. In FIG. 11A, filaments 350 have a square cross-section with sides S1 wide (or a diamond shaped cross-section if rotated 90°). In one example, S1 is about 1 to 3 inches. In FIG. 11B, filaments 350 have a circular cross-section of diameter D5. In one example, D5 is about 1 to 3 inches. In FIG. 11C, filaments 350 have an ellipsoidal cross-section. Filaments with other cross-sectional shapes such as rectangular or polygonal may be used as well.

Figure 12A:
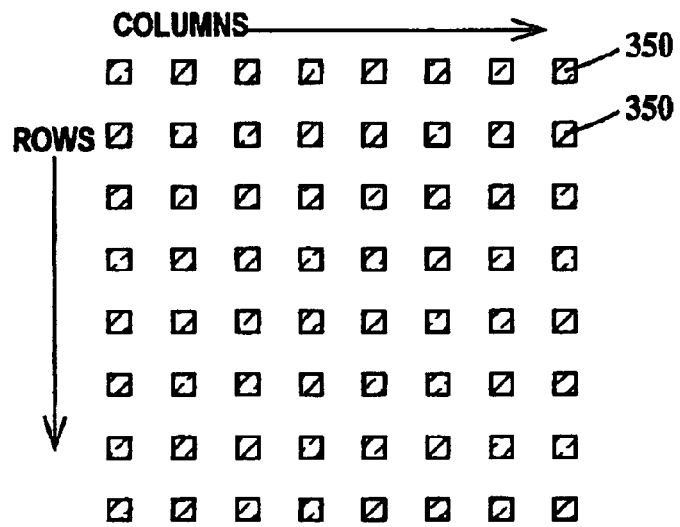
FIGS. 12A and 12B are end views illustrating alternative arrangements of the filaments in FIGS. 7, 8, 9 and 10 when viewed from the ends of the filaments.
Figure 12B:
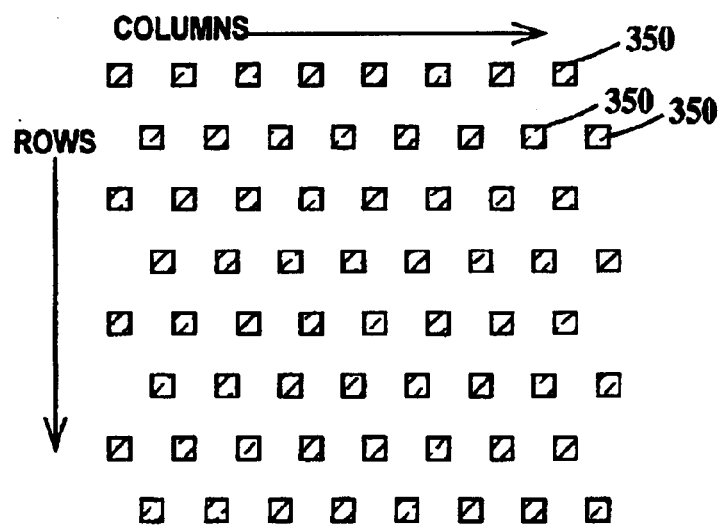

FIGS. 12A and 12B are end views illustrating alternative arrangements of filaments 350 in FIGS. 7, 8, 9 and 10 when viewed from the ends of the filaments. In FIG. 12A, filaments 350 extend in a matrix of rows (rows extend down into the tank) and columns (columns extend across the tank). Each filament 350 in each higher row is approximately aligned above another filament in a lower row. In FIG. 12B, filaments 350 extend in a matrix of rows (rows extend down into the tank) and columns (columns extend across the tank). Alternate rows of filaments 350 are staggered so each filament 350 in each higher row is approximately aligned between filaments in a lower row.

Filaments 350 may be formed from plastic such as ABS (acrylonitrile-butadiene-styrene co-polymer), PVC (polyvinyl chloride), other plastics, wood, bamboo or a fine wire, plastic or fiberglass mesh. The surface of filaments 350 should be rough or porous on a micro scale to provide a good substrate for bacteria growth.

FIG. 13 is a cross-sectional side view of the tank portion of the anaerobic digester and FIG. 14 is a top cross-sectional view through line 14—14 of FIG. 13. illustrating an alternative method of enhanced bacteria growth according to the present invention. Suspended in second chamber 130B of tank 105 is a filament rack 355. Filament rack 355 is inclined at an angle of A5 relative to second radiant floor 125B. In one example, A5 is up to about 60°. Filament rack 355 is inclined to reduce the amount of solids from slurry 160 that individual filaments 360 collect. Filaments 360 provide a substrate for colonization by naturally occurring bacteria found in slurry 160. Filaments 360 may be formed from plastic such as ABS (acrylonitrile-butadiene-styrene co-polymer), PVC (polyvinyl chloride), other plastics, wood, bamboo or a fine wire, plastic or fiberglass mesh. The surface of filaments 360 should be rough or porous on a micro scale to provide a good substrate for bacteria growth. Filaments 360 may have any of the shapes illustrated in FIGS. 11A, 11B and 11C and described supra.

FIG. 15 is an isometric view of a portion of the filaments 360 and frame 355 of FIGS. 13 and 14. In FIG. 15, each filament 360 is a thin board attached to a side 365 of rack 355. Filaments 360 may be replaced by rods, several rods replacing and individual board.

While tank 105 is illustrated using angled input and output pipes 290A and 290B respectively, the straight inlet and outlet pipes 155A and 155B respectively (see FIG. 1) may be used in conjunction with any of the filament arrangements illustrated in FIG. 7, 8, 9, 10, 11A, 11B, 11C, 12A, 12B, 13, 14 or 15 described supra.

It should be also noted, that any combination of eductors, filaments and straight and angled inlet and outlet pipes may be used.

Figure 16:
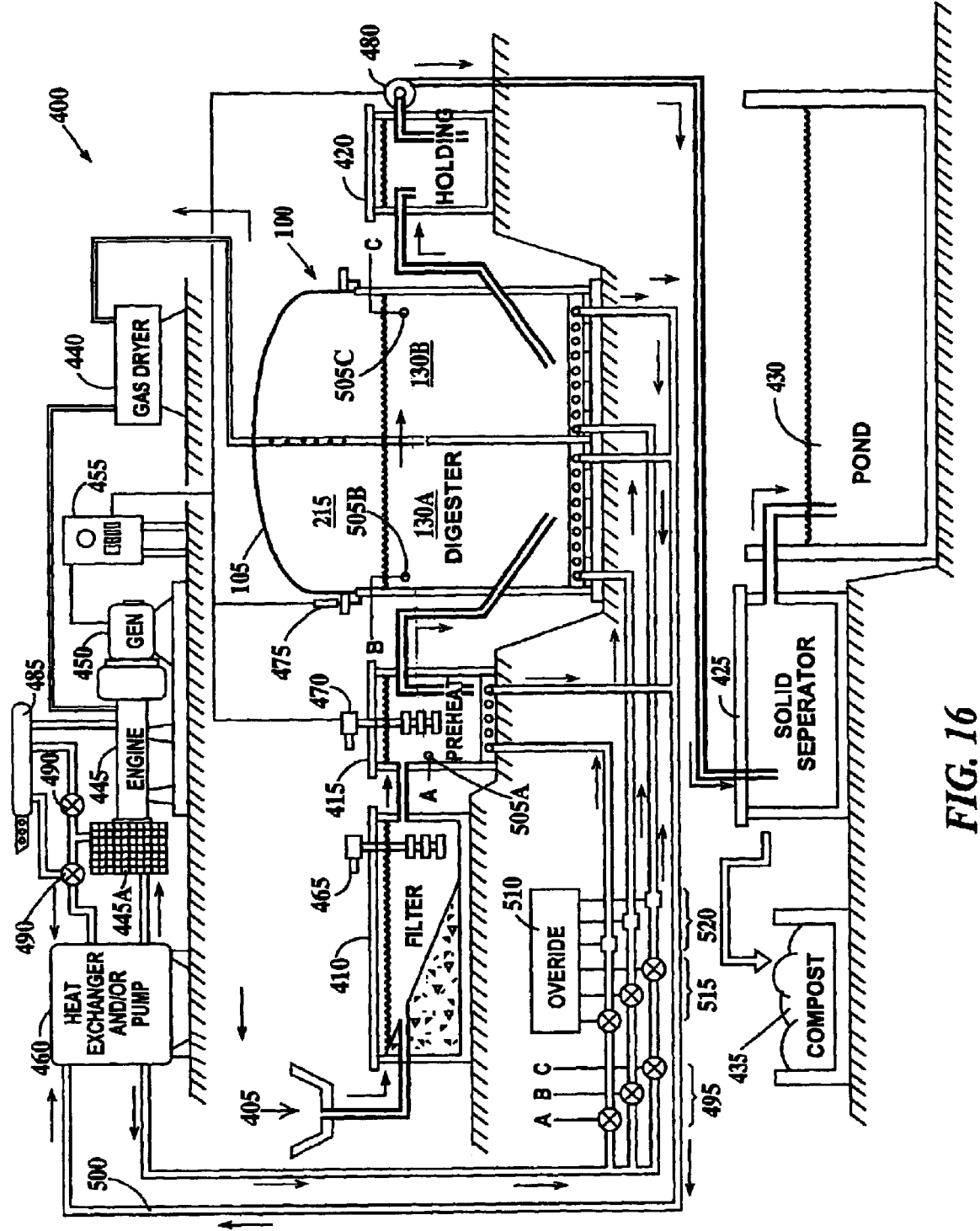
FIG. 16 is a schematic diagram of an organic waste recycling system according to the present invention.

FIG. 16 is a schematic diagram of an organic waste recycling system according to the present invention. In FIG. 16, system 400 includes a source of waste material 405 which may be an animal manure/urine mixture (or liquefied vegetable matter), a sand trap/settling tank 410, a preheat tank 415, a digester 100, a holding tank 420, a solids separator 425, a pond 430 and a composter 435. System 400 further includes a gas dryer 440, a methane fueled engine 445 having a radiator 445A, a generator 450, an electrical control panel 455 and a heat exchanger/pump 460. Heat exchanger/pump 460 may be a combination heat exchanger and pump or simply a pump as described infra.

In operation, the waste is fed into sand trap/settling tank 410, which removes particles above a predetermined size in order to not overload the downstream components of system 400 with large particle sediment which would reduce the efficiency of the system. In one example, system 400 receives a manure/urine mixture derived from pigs which contains about 8 to 16% organic solids in suspension and a small percentage of bone particles and grit from feed that is removed by the sand trap/settling tank 410. Sand trap/settling tank 410 is fitted with a mixer 465 for keeping the solids suspended. From sand trap/settling tank 410, the waste, which will here forth be designated as a slurry, is gravity fed to preheat tank 415. Preheat tank 415 heats the slurry to a temperature of about 70° to 120° F. Preheat tank 415 may be maintained at the same, hotter, or cooler than temperature than first chamber 130A of digester 100. Preheating is accomplished by either radiant floor heating as shown or by an immersion coil. Preheat tank 415 is fitted with a mixer 470 for keeping the solids suspended. From preheat tank 415 the slurry is fed into first chamber 130A of digester 100. In first chamber 130A, liquefying bacteria convert carbohydrates, proteins and fats into soluble compounds such as sugars. Acid-forming bacteria convert these soluble compounds into volatile organic acids and carbon dioxide. First chamber 130A is maintained at a temperature of 70° F. to 120° F. as described supra. From first chamber 130A, the slurry moves to second chamber 130B. In second chamber 130B, methane-forming bacteria convert the volatile organic acids into biogas. Biogas is a mixture of methane and carbon. Second chamber 130B is maintained at a temperature of about 65° F. to 115° F. as described supra. An advantage of the dual chamber design of digester 100 is independent control of each of the two processes, liquefaction and gas generation, thus allowing a stable and maximum digestion rate and a maximum gas production rate. The gas generated collects in gas collection chamber 215. The gas pressurizes due to the floating design of top 105 of digester 100. Top 105 may be rotated by motor 475. The gas produced is about 50% to 60% methane, and 30% to 40% carbon dioxide with smaller amounts of carbon monoxide, hydrogen sulfide and trace amounts of other gases. From second chamber 130B, the now fully digested slurry flows into holding tank 420. From tank 420 the digested slurry (which is primarily fibrous material that could not be digested, violate acids not converted to gas and water) may be used a fertilizer directly or may be pumped by pump 475 to optional solids separator 425. Solids separator 425 separates the liquid and solid portions of the slurry. Solids separator 425 may be a centrifugal separator, a brush separator or a press separator. The liquid portion is stored in pond 430 for later spreading on fields as a liquid fertilizer and the solids portion placed in an aerobic composter 435 where it can be dried and bagged for use as fertilizer.

System 400 is designed to operate with a constant flow of material through the system. The amount of time slurry spends in first and second chambers 130A and 130B is the same provided the rate of slurry introduction does not vary from day to day. The faster the rate of slurry introduction, the less time will be spent digester 100 and the less biogas will be produced. For example, with a 6000-gallon tank, and 300 gallons of slurry introduced per day, the retention time (average time in digester) is 20 days. With a 4000-gallon tank, and 133 gallons introduced per, the retention time is 30 days. With a 2000-gallon tank, and 42 gallons introduced per, the retention time is 48 days. Slurry should be introduced into digester 100 at half the daily amount twice a day. System 400 is a gravity fed system, though the components are applicable to a non-gravity system by the simple addition of pumps between components. A gravity system is more efficient economically.

Returning to the operation of system 400, biogas from collection chamber 215 is fed to gas dryer 440 to remove water, and then to engine 445 where it is burned. Engine 445 drives a generator 450 for the production of electricity. The flow of electricity from generator 450 is controlled by electrical control panel 455. Some of the electricity may be used to power mixers 465 and 470, motor 475 and pump 480 as well as other equipment incidental to system 400. If system 400 is installed on a farm, excess electricity may be used around the farm and/or sold. Heat from engine 445, generated by the burning of methane from digester 100, is captured by a liquid to liquid heat exchanger within 445A.

From radiator 445A, valves 485 may direct a heat exchange liquid directly to heat exchanger/pump 460 (in warm weather) or to a gas to liquid heat exchanger within exhaust 490 of engine 445 and then to heat exchanger/pump 460 (in cold weather). In one exemplary configuration, heat exchanger/pump 460 contains a primary coil and pump connected between the heat exchanger within radiator 445A and valves 485 and a secondary coil and pump connected between zone valves 495 a return line 500 and. In a second exemplary configuration, heat exchanger 460 is just a pump with its input connected to valves 485 and its output connected to zone valves 495. In the secondary configuration, return line 500 is connected directly to the heat exchanger within radiator 445A.

There are three zone valves 495. Each zone valve is connected to a corresponding temperature thermostat 505A immersed in slurry in preheat tank 415, thermostat 505B immersed in slurry in first chamber 130A and thermostat 505C immersed in slurry in second chamber 130B. Thus the temperature of preheat tank 415, first chamber 130A and second chamber 130B may be individually controlled and maintained.

An override controller 510 connected to valves override valves 515 and temperature sensors 520 downstream of zone valves 495 operates to prioritize heating of preheat tank 415, first chamber 130A and second chamber 130B when insufficient heat is produced by engine 445 by shutting down zone lines in a programmable order using shutoff valves 515 in combination with temperature sensors 520. For example, if the temperature of the preheat tank 415 zone line as measured at temperature sensors 520 drops below a set value, the shutoff valve 515 in the second chamber zone line will close, directing more heat to preheat tank 415 and first chamber 130A. This avoids shocking first chamber 130A with cold slurry.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. Therefore, it is intended that the following claims cover all such modifications and changes as fall within the true spirit and scope of the invention.

What is claimed is:

1. An anaerobic digester for digesting a slurry of organic waste comprising:

a tank having a vertical outer side wall and a vertical lower inner wall, said outer wall and inner wall each having a top surface, a first radiant heating floor between said outer wall and a first side of said inner wall forming a first chamber and a second radiant heating floor between said outer wall and a second and opposite side of said inner wall forming a second chamber, said first radiant heating floor maintaining said slurry in said first chamber at a first temperature and said second radiant heating floor maintaining said slurry in said second chamber at a second temperature;

an inlet pipe for delivering said slurry to a lower portion of said first chamber and a outlet pipe for removing digested slurry from a lower portion of said second chamber, said slurry maintained at a depth that is greater than a height of said inner wall; and a gas collection chamber sealed to said tank along the length of said upper surface of said outer wall.

2. The anaerobic digester of claim 1, wherein said inlet and outlet pipes extend into said tank at angles of between about 30° and 90° relative to said outer wall.

3. The anaerobic digester of claim 1, wherein said gas collection chamber floats in a liquid filled slot formed in and along the entire length of said top surface of said outer wall.

4. The anaerobic digester of claim 1, wherein said outer wall is circular, said gas collection chamber is circular and said gas collection chamber is rotatable in said slot.

5. The anaerobic digester of claim 1, further including means attached to said gas collection chamber and extending into a topmost portion of said slurry for breaking up crust formed on said slurry when said gas collection chamber is rotated.

6. The anaerobic digester of claim 1, further including:

first mixing eductors adapted to mix said slurry in said first chamber, said first mixing eductors located in a lower portion of said first chamber adjacent to said outer wall and said first radiant floor and pointing at said inner wall, said first mixing eductors supplied with slurry pumped from an upper region of said first chamber; and second mixing eductors adapted to mix said slurry in said second chamber, said second mixing eductors located in a lower portion of said second chamber adjacent to said outer wall and said second radiant floor and pointing at said inner wall, said second mixing eductors supplied with slurry pumped from an upper region of said second chamber.

7. The anaerobic digester of claim 1, further including:

first sweeping eductors adapted to sweep sediment and said slurry adjacent to said first radiant floor, said first sweeping eductors located in a lower portion of said first chamber adjacent to said outer wall and said first radiant floor and pointing at said inner wall, said first sweeping eductors supplied with slurry pumped from an upper region of said first chamber; and second sweeping eductors adapted to sweep sediment and said slurry adjacent to said second radiant floor, said second sweeping eductors located in a lower portion of said second chamber adjacent to said outer wall and said second radiant floor and pointing at said inner wall, said second sweeping eductors supplied with slurry pumped from an upper region of said second chamber.

8. The anaerobic digester of claim 1, wherein said second chamber includes filaments immersed in said slurry for colonization by bacteria capable of anaerobically digesting said slurry.

9. The anaerobic digester of claim 8, wherein said filaments are connected to said sidewall or both said sidewall and said inner wall.

10. The anaerobic digester of claim 8, wherein said filaments are orientated about parallel to said second radiant floor.

11. The anaerobic digester of claim 8, wherein said filaments are all orientated in the same direction.

12. The anaerobic digester of claim 8, wherein said filaments are not all orientated in the same direction.

13. The anaerobic digester of claim 8, wherein said filaments are contained in a rack suspended in said second chamber.

14. The anaerobic digester of claim 8, wherein said filaments comprise material selected from the group consisting of acrylonitrile-butadiene-styrene co-polymer, polyvinyl chloride, other plastics, wood and bamboo.

15. The anaerobic digester of claim 8, wherein said filaments comprise a fine wire, plastic or fiberglass mesh.

16. The anaerobic digester of claim 8, wherein said filaments are square, rectangular, circular, ellipsoidal or polygonal in cross-section.

17. The anaerobic digester of claim 1, wherein a said first temperature exceeds said second temperature.

18. The anaerobic digester of claim 1, wherein said first temperature is in a temperature range that optimizes a digestion rate of said slurry by a first type of bacteria and wherein a production rate of methane is increased by maintaining said second temperature within a temperature range that optimizes a production rate of said methane produced by a second type of bacteria.

19. A method for digesting a slurry of organic waste comprising:

providing a tank having a vertical outer side wall and a vertical lower inner wall, said outer wall and inner wall each having a top surface, a first radiant heating floor between said outer wall and a first side of said inner wall forming a first chamber and a second radiant heating floor between said outer wall and a second and opposite side of said inner wall forming a second chamber, said first radiant heating floor maintaining said slurry in said first chamber at a first temperature and said second radiant heating floor maintaining said slurry in said second chamber at a second temperature;

delivering said slurry to an inlet pipe extending into a lower portion of said first chamber;

maintaining said slurry at a depth greater than a height of said inner wall;

removing digested slurry through an outlet pipe extending into a lower portion of said second chamber; and collecting biogas in a gas collection chamber sealed to said tank along the length of said upper surface of said outer wall.

20. The method of claim 19, wherein said inlet and outlet pipes extend into said tank at angles of between about 30° and 90° relative to said outer wall.

21. The method of claim 19, wherein said gas collection chamber floats in a liquid filled slot formed in and along the entire length of said top surface of said outer wall.

22. The method of claim 19, further comprising rotating said gas collection chamber in said slot in order to break up crust formed on said slurry by means attached to said gas collection chamber and extending into a topmost portion of said slurry.

23. The method of claim 19, further comprising:

providing first mixing eductors adapted to mix said slurry in said first chamber, said first mixing eductors located in a lower portion of said first chamber adjacent to said outer wall and said first radiant floor and pointing at said inner wall, said first mixing eductors supplied with slurry pumped from an upper region of said first chamber;

providing second mixing eductors adapted to mix said slurry in said second chamber, said second mixing eductors located in a lower portion of said second chamber adjacent to said outer wall and said second radiant floor and pointing at said inner wall, said second mixing eductors supplied with slurry pumped from an upper region of said second chamber;

periodically mixing said slurry in said first chamber with said first mixing eductors; and periodically mixing said slurry in said second chamber with said second mixing eductors.

24. The method of claim 19, further comprising:

providing first sweeping eductors adapted to sweep sediment and said slurry adjacent to said first radiant floor, said first sweeping eductors located in a lower portion of said first chamber adjacent to said outer wall and said first radiant floor and pointing at said inner wall, said first sweeping eductors supplied with slurry pumped from an upper region of said first chamber;

providing second sweeping eductors adapted to sweep sediment and said slurry adjacent to said second radiant floor, said second sweeping eductors located in a lower portion of said second chamber adjacent to said outer wall and said second radiant floor and pointing at said inner wall, said second sweeping eductors supplied with slurry pumped from an upper region of said second chamber;

periodically sweeping said sediment and said slurry in said first chamber with said first sweeping eductors; and periodically sweeping said sediment and said slurry in said second chamber with said second sweeping eductors.

25. The method of claim 19, further including providing filaments for colonization by bacteria capable of anaerobically digesting said slurry, said filaments immersed in said slurry in said second chamber.

26. The method of claim 25, wherein said filaments are connected to said sidewall or to both said sidewall and said inner wall.

27. The method of claim 25, wherein said filaments are orientated about parallel to said second radiant floor.

28. The method of claim 25, wherein said filaments are all orientated in the same direction.

29. The method of claim 25, wherein said filaments are not all orientated in the same direction.

30. The method of claim 25, wherein said filaments contained in a rack suspended in said second chamber.

31. The method of claim 25, wherein said filaments comprise material selected from the group consisting of acrylonitrile-butadiene-styrene co-polymer, polyvinyl chloride, other plastics, wood and bamboo.

32. The method of claim 25, wherein said filaments comprise a fine wire, plastic or fiberglass mesh.

33. The method of claim 25, wherein said filaments are square, rectangular, circular, ellipsoidal or polygonal in cross-section.

34. The method of claim 19, wherein said first temperature exceeds said second temperature.

35. The method of claim 19, said first temperature is in a temperature range that optimizes a digestion rate of said slurry by a first type of bacteria and wherein a production rate of methane is increased by maintaining said second temperature within a temperature that optimizes a production rate of said methane produced by a second type of bacteria.

36. The method of claim 19, wherein said first temperature is maintained at a temperature between about 70° F. to 120° F. and said second temperature is maintained at a temperature of between about 65° F. to 115° F.

37. The method of claim 19, wherein said second temperature is between about 5° F. to 10° F. cooler than said first temperature.

38. The method of claim 19, further including preheating said slurry before introducing said slurry into said first chamber.

39. A system for digesting a slurry of organic waste comprising:

(a) a preheat tank for preheating said slurry before introducing said slurry to a digester;

(b) said digester comprising:

a tank having a vertical outer side wall and a vertical lower inner wall, said outer wall and inner wall each having a top surface, a first radiant heating floor between said outer wall and a first side of said inner wall forming a first chamber and a second radiant heating floor between said outer wall and a second and opposite side of said inner wall forming a second chamber, said first radiant heating floor maintaining said slurry in said first chamber at a first temperature and said second radiant heating floor maintaining said slurry in said second chamber at a second temperature;

an inlet pipe for delivering said slurry to a lower portion of said first chamber and a outlet pipe for removing digested slurry from a lower portion of said second chamber, said slurry maintained at a depth that is greater than a height of said inner wall; and a gas collection chamber for collecting gas, said gas collection chamber sealed to said tank along the length of said upper surface of said outer wall;

(c) an engine coupled to a generator, said engine generating heat by burning said gas collected in said gas collection chamber and driving said generator in order to generate electricity; and (d) a heat exchanger for taking said heat generated by said engine, heating a fluid with said heat and supplying said heated fluid to said preheat tank and said first and second radiant floors.

40. The system of claim 39, further including a filter for filtering said slurry prior to slurry entering said preheat tank.

41. The system of claim 39, further including a solid separator for separating solids from liquids in digested slurry after said digested slurry is removed from said digester, said digested slurry having been formed by digestion of said slurry by said digestor.

42. The system of claim 39, wherein said inlet and outlet pipes extend into said tank at angles of between about 30° and 60° relative to said outer wall.

43. The system of claim 39, wherein said gas collection chamber smooths changes in gas pressure in said gas collection chamber by floating in a liquid filled slot formed in and along the entire length of said top surface of said outer wall and said gas collection chamber is free to move along a centrally located vertical axis of said tank while floating in said liquid in said slot.

44. The system of claim 39, wherein said gas collection chamber is rotatable in said slot.

45. The system of claim 39, wherein said digester further includes means attached to said gas collection chamber and extending into a topmost portion of said slurry for breaking up crust formed on said slurry when said top is rotated.

46. The system of claim 39, wherein said digester further includes:

first mixing eductors adapted to mix said slurry in said first chamber, said first mixing eductors located in a lower portion of said first chamber adjacent to said outer wall and said first radiant floor and pointing at said inner wall, said first mixing eductors supplied with slurry pumped from an upper region of said first chamber; and second mixing eductors adapted to mix said slurry in said second chamber, said second mixing eductors located in a lower portion of said second chamber adjacent to said outer wall and said second radiant floor and pointing at said inner wall, said second mixing eductors supplied with slurry pumped from an upper region of said second chamber.

47. The system of claim 39, wherein said digester further includes:

first sweeping eductors adapted to sweep sediment and said slurry adjacent to said first radiant floor, said first sweeping eductors located in a lower portion of said first chamber adjacent to said outer wall and said first radiant floor and pointing at said inner wall, said first sweeping eductors supplied with slurry pumped from an upper region of said first chamber; and second sweeping eductors adapted to sweep sediment and said slurry adjacent to said second radiant floor, said second sweeping eductors located in a lower portion of said second chamber adjacent to said outer wall and said second radiant floor and pointing at said inner wall, said second sweeping eductors supplied with slurry pumped from an upper region of said second chamber.

48. The system of claim 39, wherein said second chamber includes filaments immersed in said slurry for colonization by bacteria capable of anaerobically digesting said slurry.

49. The system of claim 48, wherein said filaments are connected to said sidewall or to both said sidewall and said inner wall.

50. The system of claim 48, wherein said filaments are contained in a rack suspended in said second chamber.

51. The system of claim 39, wherein said first temperature is in a temperature range that optimizes a digestion rate of said slurry by a first type of bacteria and wherein a production rate of methane is increased by maintaining said second temperature within a temperature range that optimizes a production rate of said methane produced by a second type of bacteria.

* * * * *